United States Patent [19]
Gordils et al.

[11] Patent Number: 5,741,133
[45] Date of Patent: Apr. 21, 1998

[54] APPARATUSES AND PROCESS FOR PARALLEL PLACEMENT OF BONE-INTEGRATED CYLINDRICAL TYPE IMPLANTS IN DENTISTRY

[76] Inventors: Antonio Jose Gordils, CCCT 1a. Etapa- Oficina 126-A, Piso 1, Caracas, Venezuela; Nicolas Antonio Volpe, Av. Rafael Rangel, Santa Fe Norte, Quinta San Antonio Caracas, Venezuela

[21] Appl. No.: 619,307

[22] Filed: Mar. 21, 1996

[30] Foreign Application Priority Data

Dec. 7, 1995 [VE] Venezuela ............... 2131-95

[51] Int. Cl.$^6$ ................ A61C 3/02
[52] U.S. Cl. ................... 433/76
[58] Field of Search ................ 433/76

[56] References Cited

U.S. PATENT DOCUMENTS

| | | | |
|---|---|---|---|
| 1,321,129 | 11/1919 | Schlueter | 433/76 |
| 1,321,130 | 11/1919 | Schlueter | 433/76 |
| 1,380,040 | 5/1921 | Chayes | 433/76 |
| 2,675,615 | 4/1954 | Rosenberg | 433/76 |
| 5,302,122 | 4/1994 | Milne | 433/76 |

*Primary Examiner*—John J. Wilson
*Attorney, Agent, or Firm*—Ladas & Parry

[57] ABSTRACT

An apparatus for guiding a dental instrument in drilling, in the alveolus of a patient, a second longitudinal perforation that is parallel to a first longitudinal perforation. The apparatus includes (a) a first shaft having a lower portion that is insertable into the first longitudinal perforation, an upper portion and a butt therebetween, the butt having a diameter that is greater than a diameter of the lower portion such that the butt abuts a surface of the jaw of the patient with the lower portion inserted into the first longitudinal perforation; (b) sleeve defining a longitudinal bore for receiving another shaft, the sleeve having a bottom surface and a top surface; (c) first arm for connecting the upper portion of the first shaft to the sleeve with the bore disposed parallel to the first shaft and with the bottom surface of the sleeve disposed above the butt with the first shaft in a vertical orientation such that, when the first shaft is inserted in the first perforation with the butt abutting the surface of the jaw of the patient, the bottom surface of the sleeve is spaced above the jaw; (d) a second shaft insertable into the bore; and (e) second arm means, including a second arm, for connecting an upper end of the second shaft to a head of the dental instrument such that the second arm is disposed above the top surface of the sleeve with the bore disposed in the vertical orientation and with the second shaft inserted in the bore.

7 Claims, 4 Drawing Sheets

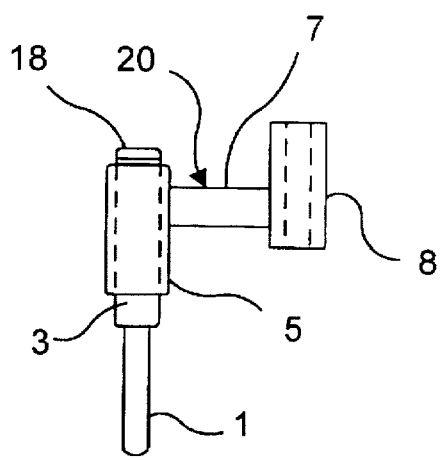
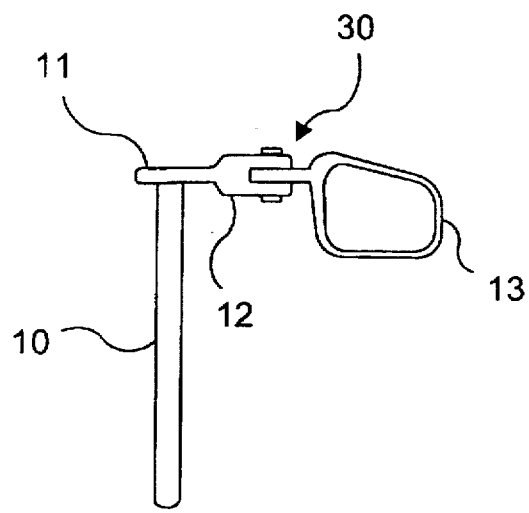
F I G. 2A
F I G. 2B
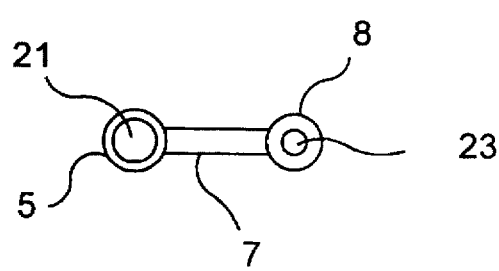
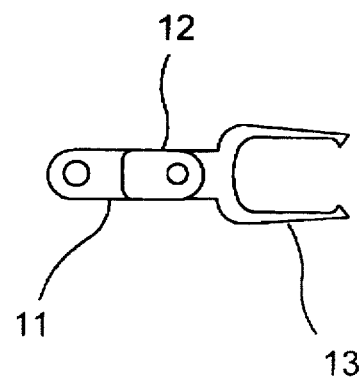
F I G. 2C
F I G. 2D

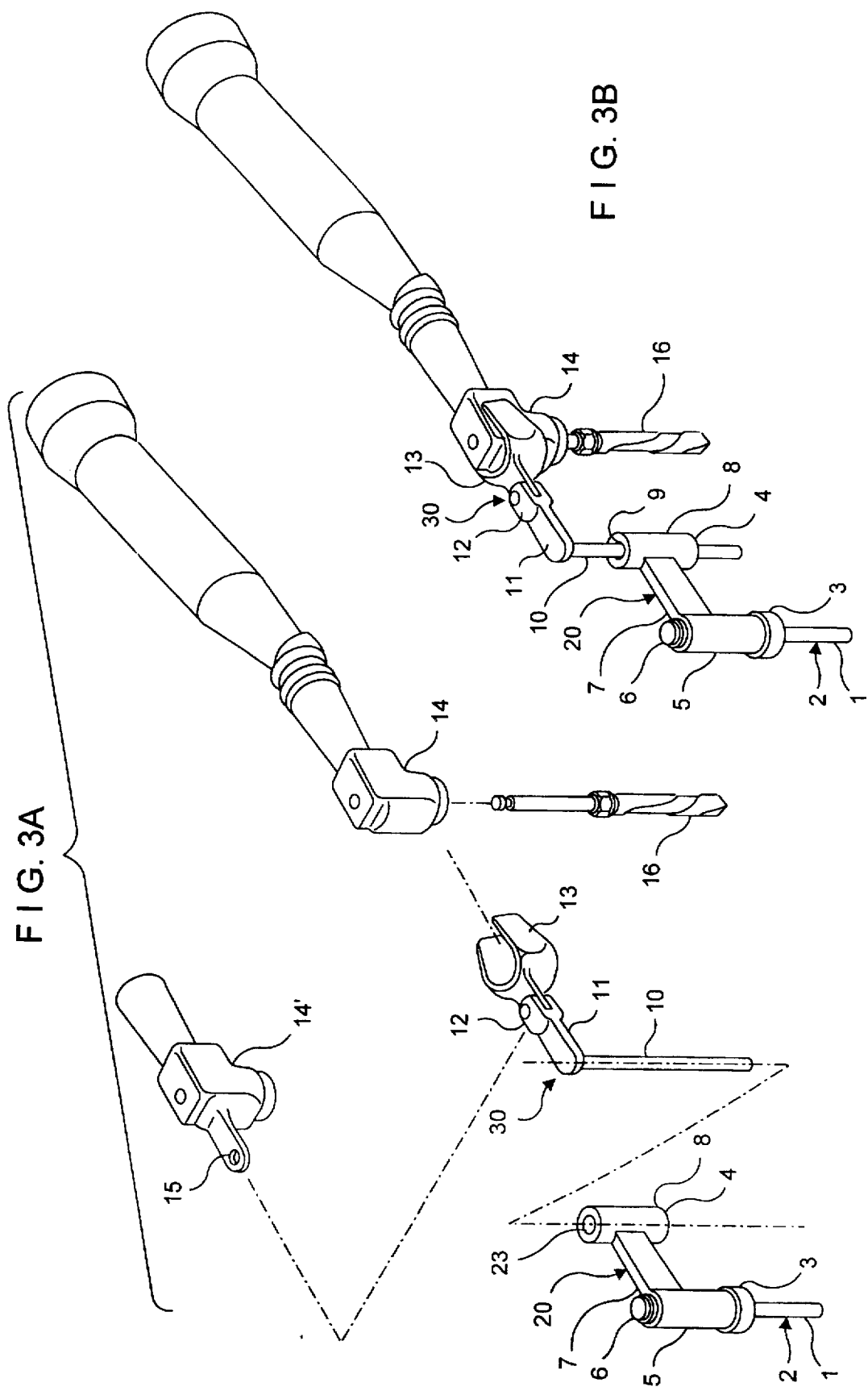

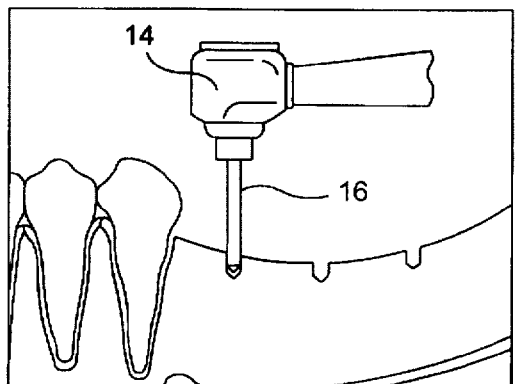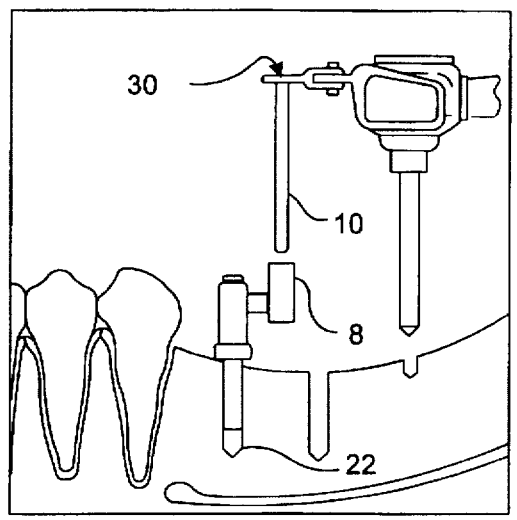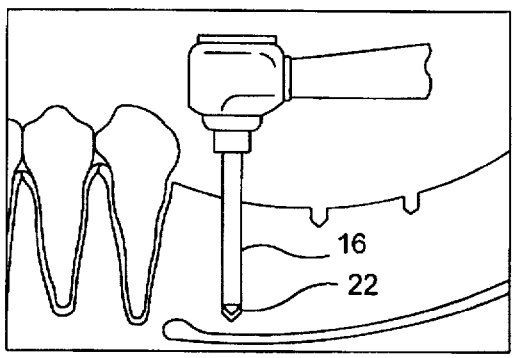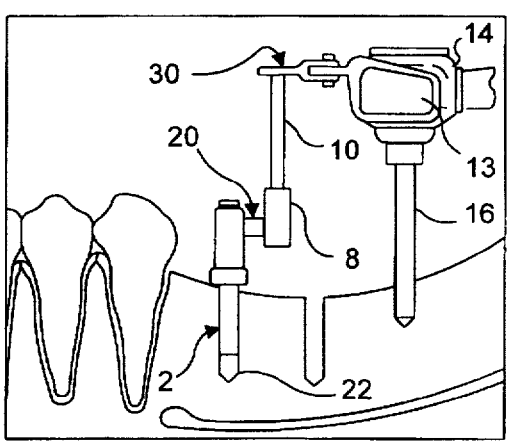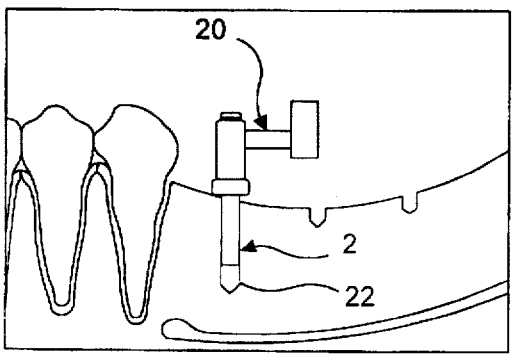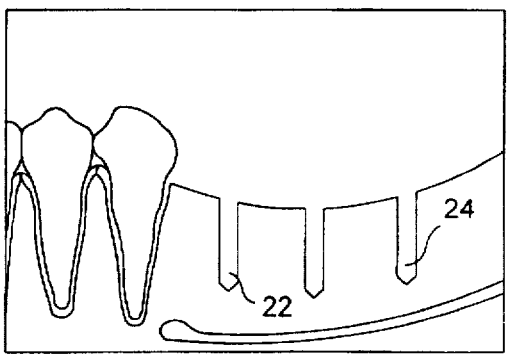
F I G. 4

APPARATUSES AND PROCESS FOR PARALLEL PLACEMENT OF BONE-INTEGRATED CYLINDRICAL TYPE IMPLANTS IN DENTISTRY

FIELD OF INVENTION

There is provided an apparatus and process for use to achieve perfect parallelism between two or more bone-integrated implants and to further reduce operating time which results in more comfort and precision for surgeons.

This invention provides a surgical method to achieve perfect parallelism when placing bone-integrated cylindrical type implants.

This invention provides an effective, safe method for parallel placement of two or more implants.

This invention reduces operating time and provides better results when making and adapting prosthetic phase.

This invention further provides better results in postoperatory evolution.

BACKGROUND

There has been a need for an apparatus to achieve perfect parallelism when surgically placing two or more cylindrical type implants, which constitutes a very frequent problem in conventional methods. Moreover, a solution has been needed for problems arising from lack of parallelism such as the need to use overstructures to place a prothesis. There have been inappropriate distributions upon occlusal loads which may cause occlusal trauma and, accordingly, possible loss of the implant. In preparation of the alveolus as in certain cases, the physical features (variable density) of the bone tissue make it difficult to achieve a uniform penetration into the surgical drill path. Furthermore, in the traditional method the path is covered by taking a visual guide as a reference, thus further making it difficult for longitudinal shafts of alveoluses to stay parallel to one another. All these problems are solved by practicing this invention as this invention provides a mechanical guide where a surgeon's precision, skills and knowledge shall play a no less important role.

Dental implants are small titanium cylinders which behave as an artificial root, and they may provide:

A method to anchor total upper and lower dentures.

A method to substitute partial dentures or total dentures for fixed bridges.

A method to replace single teeth.

STEP BY-STEP CLINICAL PROCEDURES a) Pre-Medication

Antibiotics therapy or any other medication, depending on the case.

b) Anesthesia c) Mark Position of Implant

In this step there is made a clinical, radiographic analysis with which position of implants will be determined in a study model. Later, these positions are transferred to an acrylic plate (surgical guide) marked with perforations on the alveolar rim.

d) Exposing the Alveolar Rim

An incision is made depending on the anatomy of the case, usually from 1 to 2 mm from the mucogingival joint at the mucous. Then, a total thickness flap of flesh will be raised in order to uncover the bone in the alveolar rim.

e) Location of Implants

By using the surgical guide, perforations are made in the alveolar rim with a cylindrical drill at a depth of about 1 to 2 mm. Then, by using a round drill, shriveling is done to make it easy for the following drills to enter.

f) Use of Pilot Drills

With this drill there is established the depth and alignment of the implant shaft. In this step if two or more implants are to be placed, visual aid will be secured from the parallelism pin or parallelism guide which consists of a spigot which is introduced into the first alveolus drilled by the pilot drill, it being a visual aid to place the other implants as parallel as possible.

g) Site Preparation

Regardless of the implant system being used, there will be a sequence of drills the diameters of which will gradually increase until diameter of the chosen implant is reached.

h) Implant Placement

Once the drill sequence is over, the implant will be introduced whether by pressure or bolted in the alveolus as made. Then, the flap of flesh will be stitched in place.

i) Second Operating Phase

Usually, the implant will remain uncovered from four (4) to six (6) months, and through this step soft tissues (gums) will adapt to the scarring ring which is a device bolted to the implants crown portion. Then the prosthetic phase will follow.

BRIEF DESCRIPTION OF THE DRAWINGS

FIG. 2A is a side elevational view of the first member shown in FIG. 1;

FIG. 2B is a side elevational view of the second member shown in FIG. 1;

FIG. 2C is a top plan view of a part of the first member;

FIG. 2D is a top plan view of the second member;

FIG. 3A is an exploded perspective view of the first and second members and a dental instrument with which they are used;

FIG. 3B is a perspective view of the first and second members in operational configuration attached to the dental instrument;

FIG. 4 is a schematic view showing sequential steps of a dental process in which the apparatus of the invention is used.

FIGS. 1, 2A–D and 3A–B show a first member 20 and a second member 30. The first member 20 has a shaft 2 which consists of a lower portion 1, an upper portion 18 and a butt 3. First member 20 also has a first bushing or sleeve 5 on the shaft 2, a second bushing or sleeve 8 and an arm 7 connecting the sleeve 5 with the sleeve 8. As shown in FIG. 2C, sleeves 5 and 8 define openings 21 and 23 respectively.

The second member 30 has a shaft 10, an arm 11 and a clamp 13. The arm is joined to clamp 13 by hinge 12. With reference to FIGS. 3A and 3B, it can be seen that the clamp 13 clamps on the head 14 of a dental instrument having a drill 14 thus bringing the head 14 into hinged connection with arm 11. In an alternative embodiment, the dental instrument is provided with a hinge 15. The shaft 10 of second member 30 is accommodated in the opening 23 defined by sleeve 8 of first member 20.

Figure 1:
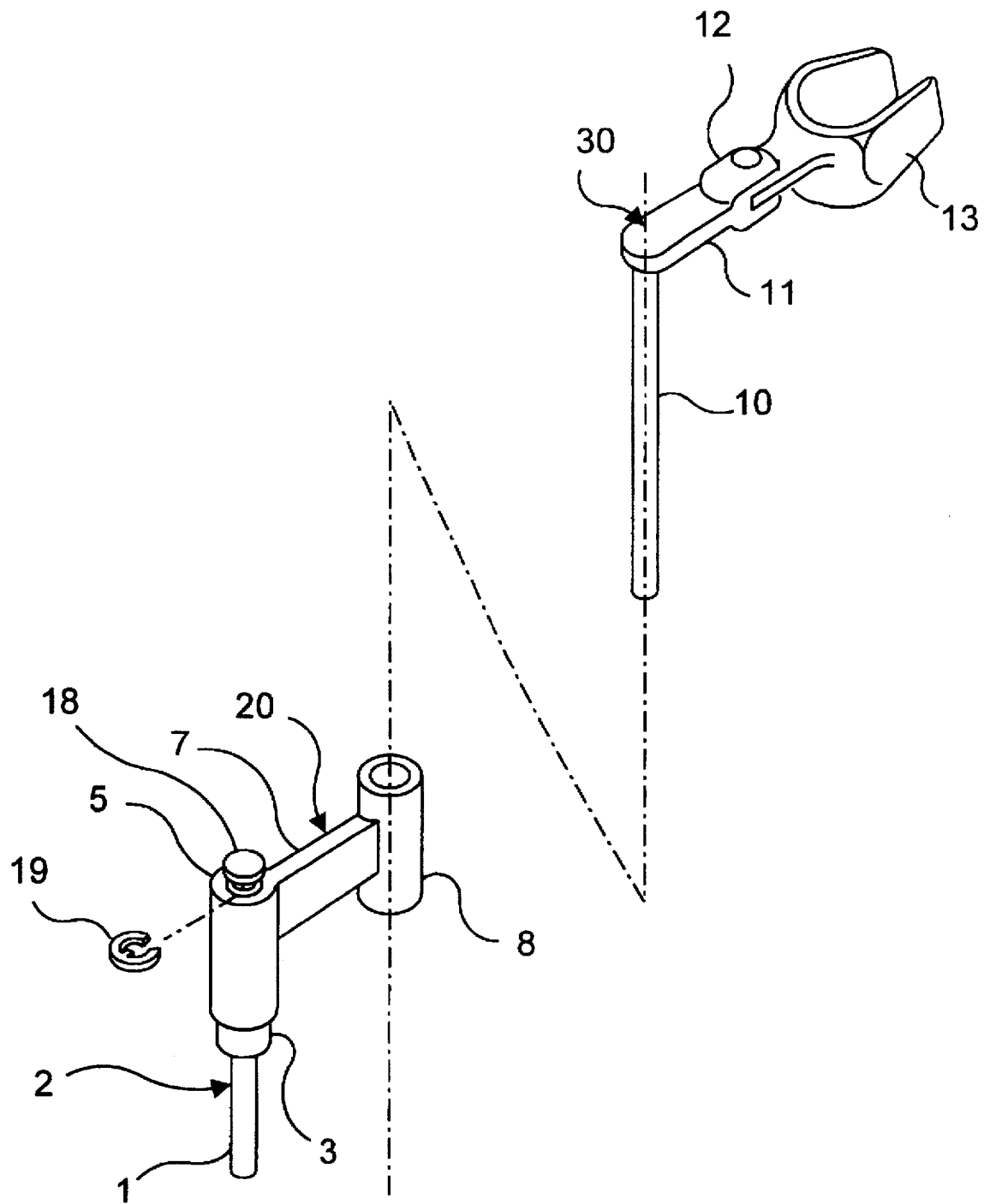
FIG. 1 is a perspective view of first and second members of an apparatus of the invention.

The aforementioned parts have specific functions related one to the others. The object is to carry, parallel to the shaft 2, an operating drill 16 which works from a counter-angle used by different motors to place bone-integrated cylindrical type implants in dentistry, which is fastened to clamp 13. This is done as follows: arm 7 has two parallel bushings 5 and 8 which allow shaft 2 to remain parallel to guide shaft 10. Arm 11 has guide shaft 10 parallel to the shaft of hinge 12, and the clamp 13 keeps the shaft of the operating drill 14 parallel to guide shaft 10. All the parts thus connected assure parallelism from the shaft 2 to the operating drill 14 in any direction to which the latter may be moved.

In FIG. 4, the use of the apparatus of the invention is shown as follows:

FIG. 4 (I) By using a cylindrical drill there are located the points chosen to place implants and with a round drill 16 shriveling is done to make it easy to position drills.

FIG. 4 (II) The first alveolus 22 is perforated according to the professional's criterion by using the first drill 16 of the sequence to widen the alveolus.

FIG. 4 (III) The shaft 2 of the first member 20 having a diameter corresponding to the completed perforation is introduced.

FIG. 4 (IV and V) On the other end of the first member 20 there is sleeve 8 for insertion of shaft 10 of second member 30. This arrangement will cause hand piece 14 to follow a path parallel to the longitudinal shaft 2 of the completed perforation 22, in such a way that the drill 16 as installed in the hand piece 14 will drill a second or more alveoluses with longitudinal shafts parallel to the first.

FIG. 4 (VI) There is shown the result achieved after using the apparatus by stressing a perfect parallelism to the longitudinal shafts 22 and 24 of the alveolus.

The conventional surgical implanting method sets forth that alveoluses should be drilled on a progressive sequence according to the diameters of the drills used until the diameter of the chosen implant is reached. This is also the case with the new process wherein, for each drill diameter, there will be a pivoting arm the shafts of which shall correspond to drill diameters. This will allow repetition of the aforesaid operation as many times as necessary to achieve such diameter as required by the chosen implant.

What is claimed is:

1. An apparatus for guiding a dental instrument in drilling, in the alveolus of a patient, a second longitudinal perforation that is parallel to a first longitudinal perforation, said apparatus comprising:
   (a) a first shaft having a lower portion that is insertable into the first longitudinal perforation, an upper portion and a butt therebetween, said butt having a diameter that is greater than a diameter of the lower portion such that the butt abuts a surface of the jaw of the patient with the lower portion inserted into the first longitudinal perforation;
   (b) a sleeve defining a longitudinal bore for receiving another shaft, said sleeve having a bottom surface and a top surface; and
   (c) first arm means, including a first arm, for connecting the upper portion of the first shaft to the sleeve with the bore disposed parallel to the first shaft and with the bottom surface of the sleeve disposed above the butt with the first shaft in a vertical orientation such that, when the first shaft is inserted in the first perforation with the butt abutting the surface of the jaw of the patient, the bottom surface of the sleeve is spaced above the jaw;
   (d) a second shaft insertable into the bore; and
   (e) second arm means, including a second arm, for connecting an upper end of the second shaft to a head of the dental instrument such that the second arm is disposed above the top surface of the sleeve with the bore disposed in the vertical orientation and with the second shaft inserted in the bore.

2. An apparatus as claimed in claim 1, wherein the second arm means comprises a clamp for detachably mounting the second member on the head of the dental instrument.

3. An apparatus as claimed in claim 2, wherein the second arm means comprises hinge means for hingedly connecting said clamp to one end of said second arm.

4. An apparatus as claimed in claim 3, wherein the first shaft, the sleeve and the first arm means comprise an integral first member.

5. An apparatus as claimed in claim 4, wherein the second shaft and the second arm means comprise an integral second member.

6. An apparatus as claimed in claim 1, wherein the first arm means comprises a second sleeve defining an opening in which the upper portion of the first shaft is accommodated and pawl means for securing the second sleeve to the first shaft.

7. A process for guiding a dental instrument in drilling, in the alveolus of a patient, a second longitudinal perforation that is parallel to a first longitudinal perforation, said process comprising the steps of:
   (i) inserting into the first longitudinal perforation a lower portion of a first member, said first member comprising
      (a) a first shaft having said lower portion, an upper portion and a butt therebetween, the lower portion having a diameter that is smaller than a diameter of the first perforation and the butt having a diameter that is greater than the diameter of the first perforation such that the butt abuts a surface of the jaw of the patient with the lower portion inserted into the first longitudinal perforation,
      (b) a sleeve defining a longitudinal bore for receiving another shaft, said sleeve having a bottom surface and a top surface; and
      (c) a first arm, connecting the upper portion of the first shaft to the sleeve with the bore disposed parallel to the first shaft and with the bottom surface of the sleeve disposed above the butt such that the bottom surface of the sleeve is spaced above the jaw;
   (ii) inserting into the bore a second shaft of a second member, said second member comprising said second shaft and further comprising a clamp for connecting the second member to a head of the dental instrument and a second arm connecting an upper end of the second shaft to the clamp such that the second arm is disposed above the top surface of the sleeve with the second shaft inserted in the bore;
   (iii) connecting the clamp of the second member to the bore; and
   (iv) drilling the second longitudinal perforation.

* * * * *